United States Patent [19]

Zusmanovsky

[11] Patent Number: 5,065,744
[45] Date of Patent: Nov. 19, 1991

[54] DEVICE FOR TREATMENT OF SEXUAL IMPOTENCE IN HUMAN MALES

[76] Inventor: Zinovy A. Zusmanovsky, 5 Sovetskaya ulitsa, 34, kv. 42, Leningrad, U.S.S.R.

[21] Appl. No.: 678,284
[22] PCT Filed: Jun. 16, 1989
[86] PCT No.: PCT/SU89/00165
§ 371 Date: Apr. 12, 1991
§ 102(e) Date: Apr. 12, 1991
[87] PCT Pub. No.: WO90/15583
PCT Pub. Date: Dec. 27, 1990

[51] Int. Cl.$^5$ ............................ A61F 5/00; A61F 6/02
[52] U.S. Cl. ........................................ 128/79; 128/842
[58] Field of Search ................. 128/842, 844, 79, 918; 604/330, 347–353

[56] References Cited

FOREIGN PATENT DOCUMENTS

| 0589978 | 1/1978 | U.S.S.R. | 128/79 |
| 0884357 | 12/1961 | United Kingdom | 128/79 |
| 1144083 | 3/1969 | United Kingdom | 128/79 |

Primary Examiner—Robert A. Hafer
Assistant Examiner—Michael Brown
Attorney, Agent, or Firm—Burgess, Ryan and Wayne

[57] ABSTRACT

A device for treatment of sexual impotence in human males, having two parallel pivotally mounted rods (1) whose ends are provided with arcuate members curved towards each other and forming respectively a glans penis retainer (3) and a penile base retainer (8). The rods (1) establish two control loops (13) curved towards each other and encompassing the penis at its base, as well as at least two stimulating loops (14) curved towards each other and located in the penile active zone.

4 Claims, 2 Drawing Sheets

DEVICE FOR TREATMENT OF SEXUAL IMPOTENCE IN HUMAN MALES

TECHNICAL FIELD

The present invention relates generally to medicine and more specifically to devices for treatment of sexual impotence in human males; the invention can find application for treatment of sexual impotence in males of the psychogenic and organic origin.

BACKGROUND ART

The problem how to treat sexual impotence in human males has become of great importance for the recent time due to ever-growing loads upon the nervous system, stress conditions, world-wide deterioration of the ecologic conditions, and so on, all these factors producing an adverse effect on man's sexual potency.

In this connection a variety of curative procedures have been elaborated for treatment of sexual impotence in human males, involving a complex of measures of psychotherapeutic, physiotherapeutic, health-resort, and other nature.

However, the affection requires a prolonged and expensive treatment and individual approach to every patient, and proves to be of low avail. It is not infrequently, especially in cases of psychogenic forms of sexual impotence, relapses of the disease are possible, which necessitates repeated or new treatment courses to be performed.

Thus, diverse devices for treatment of sexual impotence in human males have been developed in the recent time. Predominantly such devices comprise a rod one of whose ends terminates in arcuate members adapted to encompass the glans penis along the coronal sulcus thereof, while the other rod end terminates in supporting segments resting against the pubis. One of the modifications of such devices is a device for treatment of sexual impotence in human males (SU, A, 589,978), comprising two parallel rods interconnected with a possibility of rotating round own axis of each rod. The ends of said rods are connected to the arcuate members which form the retainer of the glans penis and the retainer of the penile base, while the ends of the arcuate members establishing the penile base retainer are interconnected through an elastic bundle. Besides, a pair of the arcuate members forming the control retainer is provided close to the penile base retainer.

However, the above-described device, as well as other heretofore-known devices for treatment of sexual impotence in males, fails to provide maximum reliability of fixing the glans penis, inasmuch as the fittings of the front retainer are round in cross-section, whereby its area of adherence to the penile surface is minimal so that the elastic sheathing is liable to rotate, which might result in glans penis slipping off from the closed-up retainer. Another disadvantage inherent in the heretofore-known device for treatment sexual impotence in human males resides in its being incapable to provide maximally accurate individual fitting-up of the device so that the bracer can be adjusted for a smaller length only by cutting off an excess portion, which prevents restoration of the original bracer length in the case of an error.

A primary fitting-up of the device carried out on a non-erect penis might happen inadequately accurate when true penile erection arises in the course of a coitus. In the known device its adjustment is carried out by reducing the length of the elastic element, which fails to provide a correct fitting-up and causes a discomforting sensation during the sexual intercourse, thereby affecting the efficiency of treatment. In addition, a round cross-section of the glans penis retainer components might likewise inflict discomfort upon the patient in the course of penile erection due to a high specific pressure exerted on the penile tissues in the region of the sulcus of the penile corona, nor said round-cross-section can ensure a reliable fixing of the glans penis on account of too small a contact area of the arcuate members of the retainer with the skin surface of the penis, which tells extremely unfavourably on the efficacy of treatment and causes distrust of a patient to this treatment method.

DISCLOSURE OF THE INVENTION

It is an object of the present invention to provide a device for treatment of sexual impotence in human males, which would make it possible to considerably curtail the treatment course and to render it more efficacious and reliable.

The foregoing object is accomplished due to the fact that a device for treatment of sexual impotence in human males, comprising two parallel pivotally mounted interconnected rods, one ends of which are connected respectively to aroute members curved towards each other so as to form a glans penis retainer, while the other ends of said rods are rigidly connected to the respective arcuate members curved towards each other so as to establish a penile base retainer, while the free ends of said members are interconnected through an adjustable-length elastic bundle, said rods forming at least two control loops curved towards each other and located close to the penile base retainer so as to encompass the penis at its base, according to the invention, the parallel pivotally mounted rods form at least two additional stimulating loops curved towards each other and located in the penile active zone.

Such a construction arrangement of the device provides for maximally approximation of a sexual intercourse to the natural one, i.e., renders the process of a coitus more physiologically natural.

It is expedient that each loop have at least one isolated section.

Said feature enables one, with the same arm of a lever defined by the sections with respect to the longitudinal rods, to considerably increase rated longitudinal rigidity of the device.

The device may be provided with at least two centring muffs encompassing both of the parallel pivotally mounted rods at the place of their connection to the arcuate members.

Said feature provides for high operating reliability of the device and hence patient's confidence, which contributes to his fastest rehabilitation.

It is practicable that the arcuate members forming the glans penis retainer and the penile base retainer be shaped as curved perforated plates.

Said feature makes it possible to reduce the mass of the construction itself of the device, which also adds to the efficacy of the treatment process.

In addition, provision of a perforation prevents the elastic covering from rotation and facilitates accurate fitting-up of the device for every particular patient.

BRIEF DESCRIPTION OF THE DRAWINGS

In what follows the herein-proposed device for treatment of sexual impotence in human males is illustrated by consideration of specific exemplary embodiments thereof with reference to the accompanying drawings, wherein.

BEST MODE OF CARRYING OUT THE INVENTION

Figure 1:
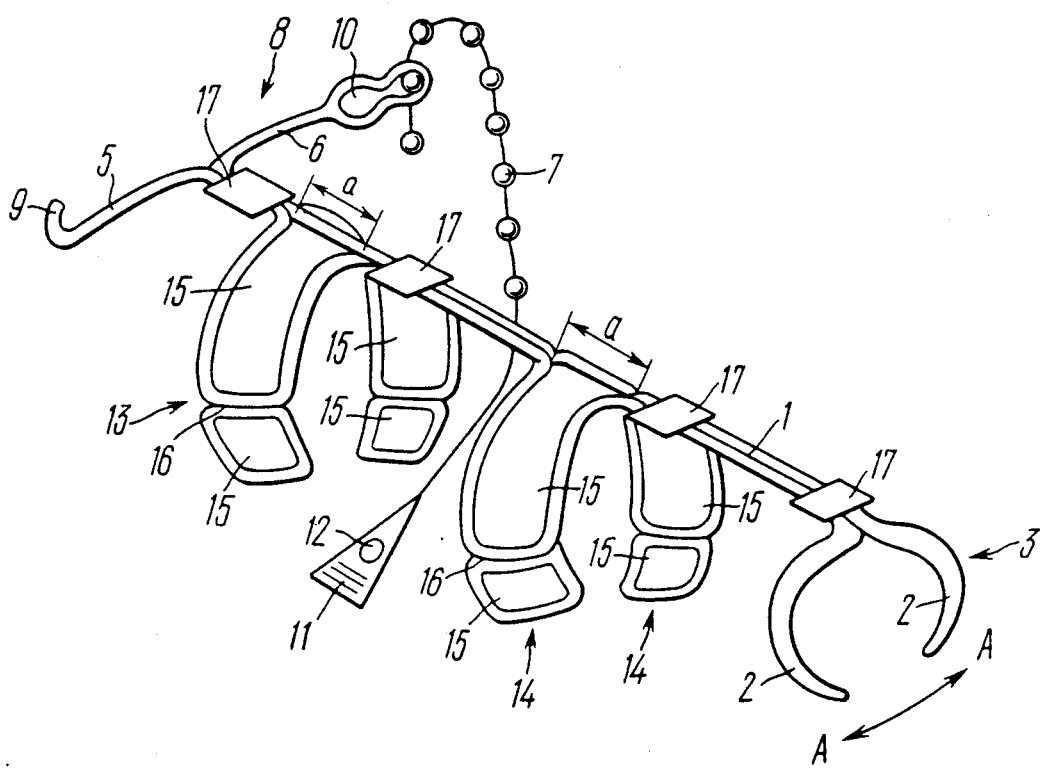
FIG. 1 is a general schematic view of a device for treatment of sexual impotence in human males, according to the invention.
Figure 2:
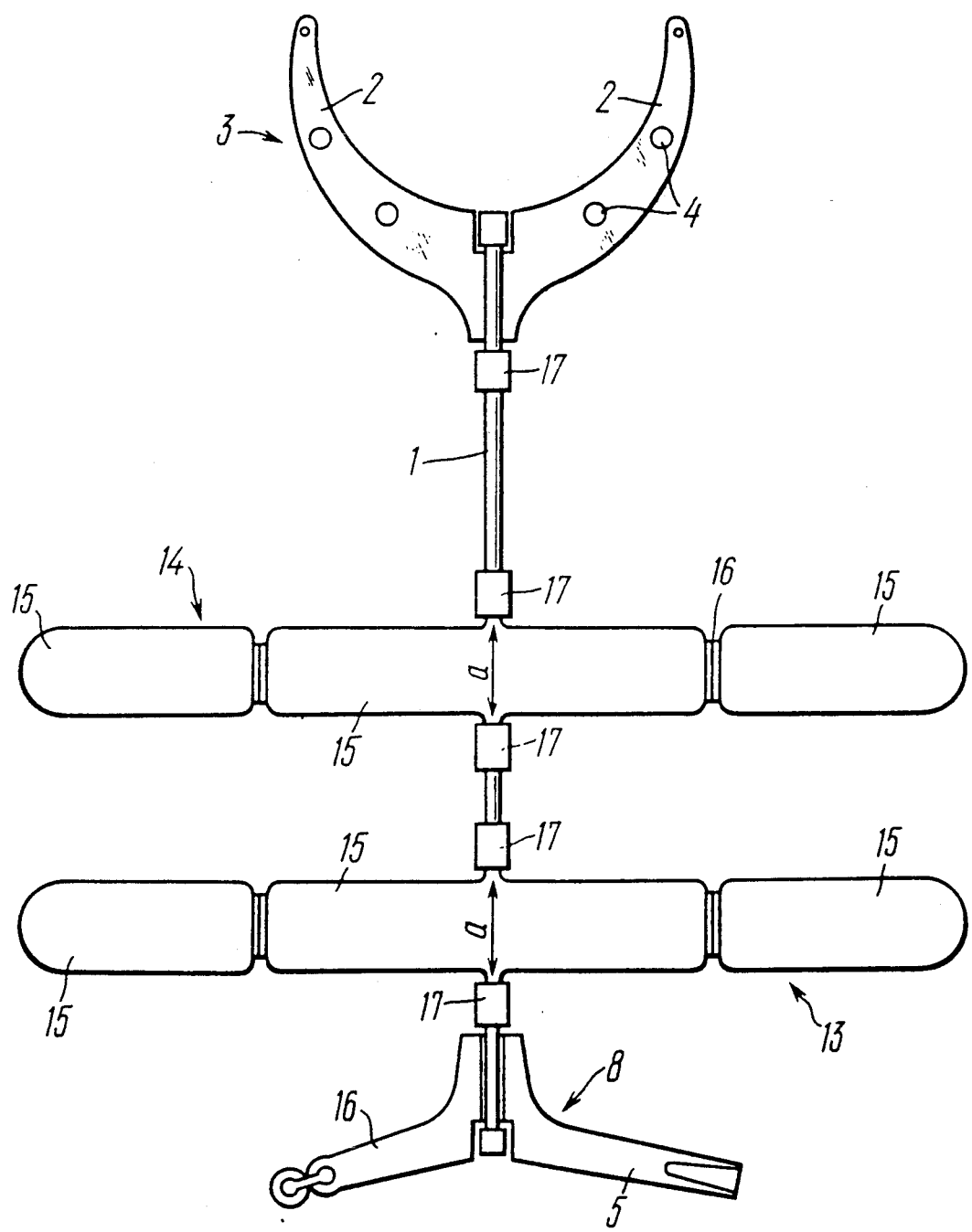
FIG. 2 is a schematic developed view of a device for treatment of sexual impotence in human males, according to the invention.

The herein-proposed device for treatment of sexual impotence in human males comprises two parallel rods 1 (FIGS. 1, 2), which may be made, e.g., of a metallic wire, which in turn may have an elastic coating. One end of each rod 1 is associated with an arcuate member 2. The arcuate members 2 of each rod 1 are curved towards each other and form in combination with each other a glans penis retainer 3. Each of the arcuate members 2 is essentially a plate curved to follow the shape of the glans penic coronal sulcus. Each of the plates may have a perforation in the form of holes 4 (FIG. 2). The other end of each rod 1 is associated to another arcuate member 5 or 6, respectively. The members 5 and 6 in combination with an elastic bundle 7 (FIG. 1), which may be made of, e.g., rubber, establish a penile base retainer 8.

The free end of the arcuate member 5 has a hook 9, whereas the free end of the other arcuate member 6 has a double eyelet 10 into which one of the ends of the adjustable-length elastic bundle 7 is passed. The elastic bundle 7 may be made of rubber and presents alternatively arranged thickenings and thinnings. The bundle 7 terminates in a holder 11 provided with an opening 12, which is to be put on the hook 9 of the arcuate member 5. The double eyelet 10 of the other arcuate member 6 is in fact two holes of different diameters interconnected through a recess. As a result of such a construction arrangement of the eyelet 10 the bundle 7 is adjustable for length within the segment confined between the two adjacent thickenings passed through the larger-diameter hole of the eyelet 10 and then through the recess, whereupon they are fixed in place in the smaller-diameter hole of the eyelet 10, a feature that simplifies much an individual fitting-up of the device.

The rods 1 establish two control loops 13 close to the penile base retainer 8, said loops being curved towards each other and encompassing the penis at its base.

Besides, the rods 1 form at least two stimulating loops 14 curved towards each other and situated in the active zone of the penis. Some more pairs of the stimulating loops 14 may be arranged in the penile active zone to suit individual features of a patient, thus simplifying preliminary individual fitting-up of the device in every particular case.

Provision of several pairs of the stimulating loops 14 in the penile active zone imparts elastic properties to the entire device due to flexibility of its middle portion.

In addition, compression of the external veins of the penile active zone by the stimulating loops 14 contributes to the blood flow regulation, that is, prevents blood outflow throughout the penile length when the device is being put onto the penis and at the beginning stage of a coitus, which to a great extent conduces to the onset of primary erection that is further reinforced by virtue of a reflex and hence expedites patient's recovery.

Each loop 13, 14 may have at least one isolated section 15 partitioned off from the rest of the interior space with a web 16. The parallel rods 1 are interconnected through at least two muffs 17, which are most expedient to be situated close to the connection of said rods 1 to the arcuate members 5 and 6, i.e., in such a manner that at least one muff 17 be located in a close proximity to each of the connection of the rods 1 to the arcuate members 5, 6 and/or at least one muff 17 be additionally placed close to the control loops 13 and the stimulating loops 14. Each muff 17 is so fitted on the rods 1 that it is rigidly coupled to one of said rods 1, whereas the other rod 1 can rotate round its longitudinal axis and round the other rod 1 rigidly coupled to the muff 17. This provides for reliable fixing of mutual arrangement of the rods 1 in an axial direction and at the same time rules out their radial displacement.

The rest of the muffs are rigidly coupled to the same rod.

The device functions as follows.

The device is fitted over a non-erect penis. The glans penis retainer 3 encompasses the sulous of the glans penis corona with the arcuate members 2, the loops 13, 14 do so with the penile middle portion, while the penile base retainer 8 encompasses the radix penis behind the scrotum at the pubic bone through its arcuate members 5, 6 and the elastic member (rubber bundle) 7. As a result, the opening 12 of the elastic member 7 is fitted, with its holder 11, onto the hook 9 of the arcuate member 5, while the degree of tension of the elastic member 7 is adjusted by properly selecting a spheroid thickening passed into the double eyelet 10.

Since the width 'a' of each loop 13, 14 is freely adjustable within broad limits, this enables one to easily carry out preliminary individual fitting-up of the device for treatment of sexual impotence in human males in every particular case, which is of special importance in cases of psychogenic origin of the disease, and at the same time to impart elasticity to the entire device.

Thus, the penis acquires the position that enables the patient to perform a coitus without any sensation of discomfort for both partners.

When true erection occurs during a sexual intercourse the penis is diametrically enlarged and exerts pressure on the control loops 13 and the stimulating loops 14, thus setting them apart. The rod 1 rigidly coupled to the muff 17 is free to turn round the axis of the other rod 1 movably mounted in said muff (in the direction facing the arrows A—A), together with said muff and hence causes the arcuate members 2 of the glans penis retainer 3 to rotate in the same direction, thus releasing the glans penis from the action of said arcuate members. This ensures unobstructed enlargement of the penis to its natural erect size (both for length and diameter) without offering any discomfort for the male partner, thus rendering the process of a coitus more physiologically natural.

In this case the isolated sections 15 of each of the loops 13, 14 perform dampening functions in response to changes in the linear dimensions of the device in the course of the sexual act. Besides, separation of the loops 13, 14 into individual sections 15 makes it possible to decrease losses in the effort translated from the radix penis to the glans penis, i.e., from the preceding loops to the following ones, since the effort is relayed through the top sections only, while the bottom sections serve for complete encompassing of the penis, its fixing and setting the entire retainer apart as soon as true erection occurs.

Whenever erection abates during coitus due to the fact that the elastic member 7 of the penile base retainer 8, when fitted over the penis, is in somewhat stretched-out state, said elastic member 7 causes the glans penis retainer 3 and loops 13, 14 formed by the rod 1, to return synchronously to the initial position, thus holding the penis in the erect position and enables one to continue the coitus. The same functional mechanism of the device makes continuation of the coitus possible in the case of ejaculation praecox.

The width 'a' of each loop 13, 14 makes it possible to readily compensate for either increased or reduced linear dimensions of the device in the course of a coitus, at the same time adding to the flexibility of the device as a whole. The loops 13, 14 opening with their top sections 15 located above the web 16, towards the rods 1 allow one not only to relay easily and rapidly an effort from the penile base retainer 8 therealong to the glans penis retainer 3 but also to return quickly the device to the initial position in the case of a zero tension force. Thus, the device operates on the feedback principle, since it monitors, as it were, itself the degree of dilation of the penile corpora cavernosa, thus establishing automatically the favourable conditions for the penis to enlarge both in length and diameter during true erection that occurs in the course of a coitus and offering no discomfort, which in turn creates an effect of absence of a sex aid device. The device, according to the invention, holds the penis in position when its effect weakens in the course of the sexual act or after premature ejaculation, as well as renders a coitus practicable even in cases where the patient is completely devoid of effective potentia coeundi. When fitted up correctly to a given patient the device enables him to enjoy harmonious intimacy practically whenever necessary.

It must be emphasized that arrangement of the stimulating loops 14 in the penile active zone is capable of producing a concomitant effect, since the aforesaid loops are situated throughout the length of the penile portion in active contact with female's genital organs in the course of a coitus. The walls of the stimulating loops 14 form a cristate surface, as it were, which provides for a normal level of stimulation of female genitalia, thus compensating for reduced sexual abilities of an inadequately erected penis. Taking account of the fact that ever-growing loads upon the nervous system and stress conditions produce a harmful effect upon sexual potency and activity of not only males but also of females, causing frigidity, practical application of the proposed device for treatment of sexual impotence in human males, which possesses also such a significant concomitant effect, becomes of paramount importance.

INDUSTRIAL APPLICABILITY

The proposed invention is especially efficiently applicable for treatment of sexual impotence in human males, predominantly of the functional (psychogenic) and functional-organic origin.

I claim:

1. A device for treatment of sexual impotence in human males, comprising two parallel pivotally mounted interconnected rods (1), a first set of ends of said rods which are rigidly connected respectively to arcuate members (2) curved towards each other so as to form a glans penis retainer (3), while the other ends of said rods are also rigidly connected to the respective arcuate members (5, 6) curved towards each other so as to establish a penile base retainer (8), while free ends of said members are interconnected through an adjustable-length elastic bundle (7), said rods (1) forming at least two control loops (13) curved towards each other and located close to the penile base retainer (8) so as to encompass the penis at its base, characterized in that the parallel pivotally mounted rods (1) form at least two stimulating loops (14) curved towards each other and located in the penile active zone.

2. A device for treatment of sexual impotence in human males as claimed in claim 1, characterized in that each of the loops (13, 14) has at least one isolated section (15).

3. A device for treatment of sexual impotence in human males as claimed in claim 1, characterized in that it comprises at least two centring muffs (17) encompassing both of the parallel pivotally mounted rods (1) proximal to the place of their connection to the arcuate members (2, 5, 6).

4. A device for treatment of sexual impotence in human males as claimed in claim 1, characterized in that the arcuate members (2) curved towards each other and form the glans penis retainer and the penile base retainer (3) which are shaped as perforated plates.

* * * * *